United States Patent [19]

Scherm et al.

[11] Patent Number: 4,758,581
[45] Date of Patent: Jul. 19, 1988

[54] PYRIDYL N-OXIDES

[75] Inventors: Arthur Scherm, Bad Homburg; Klaus Hummel, Humbololsterass; Dezsoe Peteri, Breunigweiler; Wolfgang Schatton, Eschborn, all of Fed. Rep. of Germany

[73] Assignee: Merz + Co. GmbH & Co., Frankfurt an Main, Fed. Rep. of Germany

[21] Appl. No.: 102,025

[22] Filed: Sep. 29, 1987

Related U.S. Application Data

[63] Continuation of Ser. No. 603,602, Apr. 25, 1984, abandoned.

[30] Foreign Application Priority Data

May 2, 1983 [DE] Fed. Rep. of Germany ....... 3315877

[51] Int. Cl.$^4$ .................. C07D 213/89; A61K 31/465
[52] U.S. Cl. ..................................... 514/356; 546/322
[58] Field of Search ........................ 546/322; 514/356

[56] References Cited

U.S. PATENT DOCUMENTS 3,622,587 11/1971 Carlson et al. ...................... 546/322
4,321,268 3/1982 Scherm et al. ...................... 514/356

OTHER PUBLICATIONS

Bickel Pharmacological Reviews 1969, vol. 21, No. 4, pp. 325, 333, 340.
G. J. Miller, "Plasma-High-Density-Lipoprotein Concentration and Devlopment or Ischaemic Heart-Disease", The Lancet, Jan. 4, 1975.
G. V. H. Bradby, et al., "Serum High-Density Lipoproteins in Peripheral Vascular Disease", The Lancet, Dec. 16, 1978.
James J. Maciejko, Ph.D., et al.; "Apolipoprotein A-I as a Marker of Angiographically Assessed Coronary-Artery Disease", The New England Journal of Medicine, vol. 309, Aug. 18, 1983, No. 7.
Norman E. Miller, "Induction of Low Density Lipoprotein Receptor Synthesis by High Density Lipoprotein in Cultures of Human Skin Fibroblasts", Biochemica et Biophysica Acta, 529 (1978) 131–137.
Michael S. Brown, et al., "The Cholesteryl Ester Cycle in Macrophage Foam Cells, The Journal of Biological Chemistry, vol. 255, No. 19, Oct. 10, pp. 9344–9352, 1980.
John F. Oram, et al., "The Effects of Subfractions of High Density Lipoprotein on Cholesterol Efflux from Cultured Fibroblasts", The Journal of Biological Chemistry, vol. 256, No. 16, Aug. 25, 1981, pp. 8348–8356.
George H. Rothblat, et al., "Mechanism of Cholesterol Efflux from Cells", The Journal of Biological Chemistry, vol. 257, No. 9, May 10, 1982, pp. 4775–4782.
Rebecca J. Daniels, et al., "Studies on the Rate of Efflux of Cholesterol from Cultured Human Skin Fibroblasts", The Journal of Biological Chemistry, vol. 256, No. 10, May 25, 1981, pp. 4978–4983.
O. Stein, et al., "Cholesterol Content & Sterol Synthesis in Human Skin Fibroblasts & Rat Aortic Smooth Muscle Cells Exposed to Lipoprotein-Depleted Serum & High Density Apolipoprotein/Phospholipid Mixtures", Biochimica et Biophysica Acta, 431 (1976) 347–358.
D. Reichl, et al., "Evidence for the Presence of Tissue--Free Cholesterol in Low Density & High Density Lipoproteins of Human Peripheral Lymph", Atherosclerosis, 37 (1980) 489–495.
L. K. Miller, et al., "Side-Chain Oxidation of Lipoprotein-Bound [24,25-$^3$H] Cholesterol in the Rat: Comparison of HDL and LDL and Implications for Bile Acid Synthesis", Journal of Lipid Research, vol. 23, 1982, pp. 335–343.

(List continued on next page.)

Primary Examiner—Jane T. Fan
Attorney, Agent, or Firm—Gordon W. Hueschen

[57] ABSTRACT

N-oxides of pyridyl carboxylic acid esters of the following formula are described:

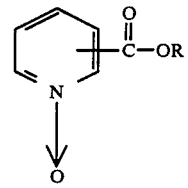

wherein R is

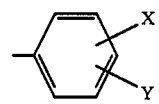

wherein X is a hydrogen atom, straight or branched $C_1$–$C_5$-alkyl, $C_5$–$C_{12}$-cycloalkyl, 1-adamantyl, or cyclohexylacetyl, and
wherein Y is a hydrogen atom, straight or branched $C_1$–$C_5$-alkyl, 2-ethylbenzofuranoyl-3, $C_5$–$C_{12}$-cycloalkyl, or 2-[(4-chlorophenoxy)-2-methylpropanoyloxy]ethyl;
a process for the manufacture thereof, pharmaceutical compositions containing these compounds, and method of using the same. These compounds are suited for use in the treatment of hyperlipidemas.

3 Claims, No Drawings

OTHER PUBLICATIONS

Von P. Röschlau, et al., "Enzymatische Bestimmung Des Gesamt-Cholesterol Im Serum", *Z. Klin. Chem. Klun. Biochem.*, 12 Jg. 1974, S. 403–407.

Thomas P. Bersot, et al., "Lipoprotein Receptors in Lipid Transport & Artherogenesis", *Artherosclerosis: Mechanisms and Approaches to Therapy*, Raven Press, New York, 1983, pp. 143–152.

Tatu A. Miettinen, et al., "Effect of Long-Term Antihypertensive & Hypolipidemic Treatment on High Density Lipoprotein Cholesterol & Apolipoproteins A-I and A-II", Atherosclerosis, 36 (1980) 249–259.

Fiedler, "Die Pharmazie", vol. 20, No. 7, pp. 401–404 (Jul. 1965) and certified translation into English.

Fiedler, Chem. Abs. 63, 11486e (1965).

Fiedler, Chem. Abs. Index, 3790F and C18H19N02S (1965).

Prino et al., "Antithrombotic Activity of Polydesoxynucleotidic-Like Substance (Fraction P), *Advances in Coagulation, Fibrinolysis, Platelet Aggregation and Atherosclerosis* 1976, pp. 282–289.

Subissi et al., "Acute Effects on Plasma Lipids in the Rat of a New Long-Acting Nicotinic Acid Derivative: LG 13979", J. Pharm. Pharmacol. 1983, 35:571–575.

PYRIDYL N-OXIDES

This is a continuation of application Ser. No. 603,602, filed Apr. 25, 1984, now abandoned.

The present invention relates to N-oxides of pyridyl carboxylic acid esters, a process for the manufacture thereof, pharmaceutical compositions containing these compounds, and a method of using the same.

It is known that atherosclerosis is caused by the accumulation of lipids in the aorta and the coronary, cerebral, and peripheral arteries. This results in an increased risk of thromboses or artery obstruction. Dependent on the nature of the elevated plasma lipoprotein levels, either the elevated cholesterol or triglyceride level is of importance. In this connection even cholesterol levels of 200–300 mg/100 ml serum and triglyceride levels of 150–200 mg/100 ml serum are considered to be excessive.

The two most widely known active substances which have hitherto been used for the treatment of hyperlipidemas are the ethyl ester of 2-(p-chlorophenoxy)isobutyric acid—known as clofibrate, its salts, and nicotinic acid. These compounds act on the serum lipids via different modes of action. While in test animals doses of 100–500 mg/kg of body weight effect mainly a reduction of the cholesterol level in addition to a slight reduction of the free fatty acids, the administration of 3-pyridylcarbinol or nicotinic acid or its salts brings about a substantial lowering of the fatty acid level, even at low doses between 10 and 100 mg/kg. However, neither of these two substances has a significant lowering action on the triglyceride level. In addition, due to its unpleasant and known side effects (flush, headache, nausea, vomiting), nicotinic acid can only be used to a limited extent, so that therapy often must be discontinued prematurely.

Additionally, it is known that clofibrate, in fact, effects a fall of the triglyceride and pre-$\beta$-lipoprotein values to up to 50% below the initial values, this degree of lowering, however, not being achieved in the case of cholesterol. Nicotinic acid and its derivatives, on the contrary, predominantly act on elevated cholesterol and elevated fatty acid values, whereas the decrease of endogenous triglyceride resynthesis via inhibition of tissue lipolysis is only a secondary effect (cf. Negotiations of the German Association for Internal Medicine, 82nd Congress, held at Wiesbaden from Apr. 25–29, 1976, Part I, J. F. Bergmann Verlag, Munich).

The aforementioned active substances therefore have the capacity to significantly reduce the blood levels of only one lipid component, e.g., the triglycerides, while the other lipid components are therapeutically influenced only slightly or not at all. Such therapeutic effect can only be achieved by a dosage increase.

According to most recent findings in the field of lipid research, a suitable antihyperlipidemic drug should not only reduce the triglyceride and cholesterol values, but also effect an increase of the HDL lipoproteins (atherogenic protective factor), and a decrease of the LDL and VLDL lipoproteins in the course of the treatment. Additionally, proliferation of peroxisomes should not occur, so that the liver weight remains constant.

In DE-OS No. 30 09 099, nicotinic acid esters are described which, although meeting some of the foregoing requirements such as lowering of both lipid components, leave much to be desired as regards the remaining requirements.

Therefore, an objective of this invention was to provide other compounds which, in addition to their lipid-lowering action, exert—at the same dosage or even at lower dosage—a favorable influence on the other factors suited to combat atherosclerosis.

Unexpectedly, it has been found that N-oxides of pyridyl carboxylic acid esters exhibit a strong action on both elevated serum triglyceride and cholesterol values by simultaneously effecting a strong increase of the vasoprotective HDL and a reduction of the atherogenic LDL and VLDL lipoprotein values. Since the compounds according to the invention do not cause proliferation of peroxisomes, the liver weights remain essentially constant.

Therefore, the subject matter of the present invention comprises N-oxides of pyridyl carboxylic acid esters having the following formula:

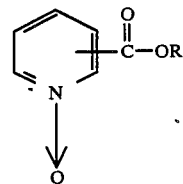

wherein R is

wherein X is a hydrogen atom, straight or branched $C_1$–$C_5$-alkyl, $C_5$–$C_{12}$-cycloalkyl, 1-adamantyl, or cyclohexylacetyl, and wherein Y is a hydrogen atom, straight or branched $C_1$–$C_5$-alkyl, 2-ethylbenzofuranoyl-3, or $C_5$–$C_{12}$-cycloalkyl, or 2-[(4-chlorophenoxy)-2-methylpropanoyloxy]ethyl; process for the manufacture thereof, pharmaceuticals containing these compounds, and the use thereof as antihyperlipidemics.

The

group may be in position 2, 3 or 4, preferably position 3. The phenyl group of R may be mono- or disubstituted, the substituent X or Y preferably being a cyclohexyl, cyclopentyl, or 2-ethylbenzofuranoyl-3 group. Examples of suitable X and Y substituents are methyl, ethyl, propyl, isopropyl, butyl, tert-butyl, sec-butyl, and pentyl groups.

The process for the manufacture of the compounds according to the invention is characterized in that a pyridyl carboxylic acid ester which is non-oxidized at the nitrogen is N-oxidized with peroxy acid or glacial acetic acid-hydrogen peroxide, according to generally known procedure, preferably in the presence of a non-reactive organic solvent, the exact solvent being non-critical.

The compounds according to the invention may be processed into pharmaceutical compositions which may contain a usual pharmaceutically-acceptable carrier or diluent in addition to the active substance. They are suited for oral and parenteral administration.

Solid preparations for oral administration are capsules, tablets, pills, powders, and granules. In such solid preparations, the active ingredient is mixed with at least one inert binding agent such as cane sugar, lactose, or starch. Additional substances such as lubricants or buffers may be present. The tablets and pills may be provided with an enteric or other coating.

For parenteral administration the compounds of the invention may be applied in the form of emulsions, solutions, and suspensions containing commonly used inert diluents such as water. Such liquid agents may also contain wetting, emulsifying, and dispersing agents as well as sweetening, flavoring, and odor-providing substances in oral forms.

Dependent on the intended mode of applicaition and duration of treatment, the dosage of the active substances in the preparations may vary. In general, a therapeutic agent suited for the treatment of hyperlipidema contains a hyperlipidemically-active dose of at least one compound according to the invention, ordinarily combined with a pharmaceutically-acceptable carrier or diluent.

lesterol levels and the initial mean cholesterol level was approximately equal for all groups.

During the following fourteen-day treatment period, all animals, with the exception of the controls, received the hypercholesterolemic diet to which the appropriate concentration of the test substance (0.1%) had been added.

During the fourteen (14) days of drug administration, the individual food consumption was recorded daily, whereas the body weights of the animals were recorded once per week.

On the last day of the study, the rats were again bled from the retro-orbital plexus at the same time as on Day Fourteen (14) of the pre-dose period.

The blood samples were again analyzed for total serum cholesterol, HDL cholesterol, $\beta$-lipoproteins, and triglyceride levels. The animals were then sacrificed, and the livers removed and weighed.

As compared with the control animals, highly significant positive changes of all parameters, except liver weights, could be observed (cf. Table 1). The liver weights remained constant.

TABLE 1

| | | Evidence of the effectiveness of the compounds according to the invention | | | | |
|---|---|---|---|---|---|---|
| Compound No. | Dosage (% in feed) | Total cholesterol mg/100 ml | HDL-cholesterol mg/100 ml | Triglycerides mg/100 ml | $\beta$-lipo-proteins optical density × 1000 | Liver weights g |
| Control animals | — | 235.6 | 22.5 | 116.3 | 341.3 | 15.3 |
| 1 | 0.1 | 184.8 | 28.5 | 121.5 | 325.8 | 16.3 |
| 2 | 0.1 | 191.5 | 26.3 | 112.1 | 318.5 | 16.0 |
| 3 | 0.1 | 145.0 | 28.3 | 108.1 | 244.4 | 15.0 |
| 4 | 0.1 | 170.1 | 25.9 | 113.7 | 307.2 | 15.2 |
| 5 | 0.1 | 150.6 | 27.4 | 109.2 | 266.3 | 15.6 |
| 6 | 0.1 | 159.1 | 28.1 | 105.9 | 254.8 | 15.1 |
| 7 | 0.1 | 155.1 | 27.2 | 109.8 | 260.3 | 15.4 |

EVIDENCE OF EFFECTIVENESS

Method

Female CFY rats (50 to 60 g) were obtained from Hacking and Churchill Ltd. On arrival, each animal was weighed and placed in an individual wire mesh cage and given a four-day acclimatization period.

The room temperature was maintained at 23° C.±2° C.; relative humidity and room temperature were recorded daily and lighting was controlled to give 12 hours light (7 a.m. to 7 p.m.) and 12 hours dark per 24 hours.

Throughout the study the animals received water ad libitum.

During the four-day acclimatization period, the rats were fed Spratt's powdered Laboratory Animal Diet No. 2 (low fat) ad libitum. During the following fourteen (14) days, all rats received ad libitum Spratt's powedered Laboratory Animal Diet No. 2 to which 2% (w/w) cholesterol and 1% (w/w) cholic acid had been added. During this period, the individual food consumption was recorded three (3) times per week.

Between 06.00 and 07.30 hours in the morning of the fourteenth day, a blood sample was obtained from each rat from the retro-orbital plexus under light anesthesia. All blood samples were analysed for total serum cholesterol, HDL cholesterol, $\beta$-lipoproteins, and triglyceride concentrations.

On the basis of total serum cholesterol levels, the animals were allocated to the treatment groups such that each group had a similar distribution of total cho- The following Examples are given to illustrate the present invention, but are not to be construed as limiting.

GENERAL PROCEDURE FOR THE MANUFACTURE OF PYRIDYL CARBOXYLIC ACID ESTER N-OXIDES

To an ice-cooled solution of the respective nicotinate (+) (20 mmol) in 50–100 ml of dichloroethane, stirred by means of a magnetic stirrer, 4.22 g (22 mmol) of 90% 3-chloroperbenzoic acid is added in portions over a period of fifteen (15) minutes. The solution is stirred for another thirty (30) minutes at 0° C. The additional reaction conditions can be taken from Table 2 (TLC control: SiO$_2$; CHCl$_3$/MeOH 9:1). The reaction temperature range is generally $-10°$ C. to about 60° C., with 0° C. to 40° C. being the usual optimum range.

For further processing the reaction mixture is diluted with dichloromethane to about 250 ml. The organic phase is washed with saturated Na$_2$SO$_3$ solution (2×100 ml), saturated NaHCO$_3$ solution (3×100 ml), and saturated NaCl solution (2×100 ml). After drying over Na$_2$SO$_4$, the solvent is removed under vacuum, the residue being recrystallized by using active carbon, if necessary (cf. Table 2).

Other perbenzoic acids and other peroxy acids, or hydrogen peroxide in glacial acetic acid, may be substituted for the perbenzoic acid employed, according to the skill of the art.

The following compounds were prepared according to the foregoing method:

EXAMPLES:

No.
1. 2-Cyclohexylphenylnicotinate-N-oxide
2. 4-Cyclohexylphenylnicotinate-N-oxide
3. 2-t-Butyl-4-cyclohexylphenylnicotinate-N-oxide
4. 4-(Cyclohexylacetyl)phenylnicotinate-N-oxide
5. 4-(1-Adamantyl)phenylnicotinate-N-oxide
6. 1-[2-(4-Chlorophenoxy)-2-methylpropanoyloxy]-2-(nicotinoyloxy)ethane-N-oxide
7. 4-(2-Ethylbenzofurane-3-oxo)phenylnicotinate-N-oxide Numerous additional products within the scope of the present invention are prepared in the same manner from the non-N-oxidized parent compound, e.g., those of U.S. Pat. No. 4,321,268, including especially homologues and analogues of the compound number 3, wherein another lower-alkyl group, preferably a branched-chain lower-alkyl group, having up to and including six (6) carbon atoms, including those groups earlier-mentioned as X or Y substituents, is present instead of the t-butyl group, whether in the 2 or 3 position and, of course, in such compounds the cyclohexyl group can also be varied in its position on the phenyl ring, in which case the lower-alkyl group may also accordingly be in another position on the phenyl ring, such as the 3 or 4 position.

(+) The preparation of the nicotinates of Examples 1 to 5 is described in U.S. Pat. No. 4,321,268 and in Deutsche Offenlegungsschrift No. 30 09 099. The preparation of the nicotinate of Example 6 is described in German Pat. No. 1,941,217.

(+) The starting material for the compound of Example 7 is prepared as follows:

A mixture of 0.2 ml benzarone and 0.24 ml of nicotinic acid chloride hydrochloride in 400 ml of dry pyridine are kept at room temperature for fifty (50) hours. The reaction mixture is poured onto 800 ml of ice water and extracted four (4) times with 100 ml of methylene chloride. The organic layer is washed twice with fifty (50) ml of water, dried over anhydrous $MgSO_4$ for 24 hours, and evaporated. The resulting oil is taken up in eighty (80) ml of hot ethanol. The product crystallizes on cooling, whereafter solvent is removed under vacuum and the product recrystallized from ethanol to give yellow needles having a Mp. of 83° C. in a yield of 88%.

Still other starting materials are found or prepared in accord with U.S. Pat. No. 4,321,268.

TABLE 2

Reaction conditions for the preparation of the compounds according to the invention

| Example No. | Reaction conditions | Yield | Mp. |
|---|---|---|---|
| 1 | 7 h; RT (0°–RT) | 65% | 120–122° C. (AcOEt/n-hexane) |
| 2 | 7 h; RT (0°–RT) | 55% | 199–201° C. (EtOH) |
| 3 | 16 h; RT (0°–RT) | 60% | 170–171° C. (EtOH) |
| 4 | 5 h; 0°–40° C. | 57% | 174–175° C. (EtOH) |
| 5 | 5 h; 0°–40° C. | 84% | 283° C. (decomp.) (Toluene) |
| 6 | 5 h; 0°–40° C. | 74% | 79–80° C. ($CH_2Cl_2$/diisopropyl ether) |
| 7 | 16 h; 40° C. | 58% | 125° C. |

Numerous additional N-oxide compounds of the invention are prepared in the same manner from their parent compounds, which are found or prepared in accord with U.S. Pat. No. 4,321,268.

Generally, all standard lipid-lowering agents, which are clofibrate-derivatives as well as nicotinic acid, induce proliferation of peroxisomes. Although this may be a significant part of their mechanism of action, the inducing effect upon peroxisomes generally leads to an increase in liver weight (hepactomegalie) and is even discussed as a preneoplastic transformation of liver cells by some scientific groups. In contrast, N-oxide compounds of the present invention have surprisingly been found devoid of peroxisomal-proliferating effect.

As to rebound of free fatty acids and triglycerides, when employing the standard nicotinic acid as well as certain other pyridyl carboxylic acid esters, such compounds potently reduce triglycerides and fatty acids after each consecutive single administration and for a definite period of time. However, after this beneficial effect has ceased, a sharp increase in free fatty acids and triglycerides, a so-called rebound, to levels which are very much higher than the pretreatment levels, is observed. These higher levels are associated with a considerably higher risk of atherosclerosis. Surprisingly, the N-oxides of the present invention do not produce the rebound phenomenon and therefore provide a more efficient treatment of atherosclerosis.

Further, the standard nicotinic acid, as well as certain pyridyl carboxylic acid esters, produce a slightly stimulating effect on prostacyclins, thus preventing platelet aggregation followed by atherosclerotic plaque formation. The corresponding N-oxides of the present invention, however, appear to assert their activity on prostaglandin biosynthesis in a different manner, which positively results in an additional pharmacological effect, namely, anti-edema or antiphlogistic activity. Since edema of the arterial vessel wall is considered to be the first step in atherosclerotic plaque formation, the compounds of the present invention produce an interesting anti-atherosclerotic profile as compared with their parent nicotinic acid esters. The parent compounds appear to react against atherosclerosis at a later point in time, namely, platelet aggregation, whereas the N-oxides of the present invention appear to be active already during the first step of atherogenesis, namely, against the edema of the arterial vessel wall.

Moreover, in the animal model of Gustafson and Kiessling, published in Z. Versuchstierkunde 24, 271–277 (1978), entitled "The Mouse as a Model for Evaluation of Hypotriglyceridemic Drugs", with a treatment of five (5) animals per group over a period of one (1) week with compounds of the present invention mixed into a standard diet in a concentration of three-tenths percent (0.3%), the compounds of the present invention showed increases in relative liver weight of a smaller magnitude than their parent compounds whereas, as to total cholesterol, measured in millimoles per liter, the compounds of the present invention in each case showed a lowering of the total cholesterol values of a greater magnitude than their respective parent compounds.

In conclusion, from the foregoing, it is apparent that the present invention provides novel pyridyl carboxylic acid ester N-oxides, a process for preparing the same, pharmaceutical compositions thereof as well as a method of treating hyperlipidemia therewith, all having the foregoing enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. 2-t-butyl-4-cyclohexylphenylnicotinate-N-oxide.

2. Pharmaceutical composition suitable for treating hyperlipidema containing an effective antihyperlipedemic amount of the compound according to claim 1 together with a pharmaceutically-acceptable carrier.

3. Method of treating hyperlipidema comprising the step of administering to a subject afflicted with hyperlipidema an effective antihyperlipidemic amount of the compound of claim 1, or of a composition of claim 2.

* * * * *

UNITED STATES PATENT AND TRADEMARK OFFICE
CERTIFICATE OF CORRECTION

PATENT NO. : 4,758,581

DATED : July 19, 1988

INVENTOR(S) : Arthur Scherm, Klaus Hummel, Dezsoe Peteri and Wolfgang Schatton

It is certified that error appears in the above-identified patent and that said Letters Patent is hereby corrected as shown below:

Title Page, [73] Assignee:, line 2; "an Main" should read -- (Main) --.

Col. 3, line 15; "applicaition" should read -- application --

Col. 3, line 56; "powedered" should read -- powdered --

Signed and Sealed this

Tenth Day of January, 1989

Attest:

DONALD J. QUIGG

Attesting Officer

Commissioner of Patents and Trademarks